United States Patent
Lv et al.

(10) Patent No.: US 11,123,508 B2
(45) Date of Patent: Sep. 21, 2021

(54) OXYGEN GENERATOR FOR RESPIRATION-SYNCHRONIZED OXYGEN SUPPLY

(71) Applicant: SHENZHEN WINPOWER TECHNOLOGY CO., LTD., Shenzhen (CN)

(72) Inventors: Heqi Lv, Shenzhen (CN); Ming Li, Shenzhen (CN)

( * ) Notice: Subject to any disclaimer, the term of this patent is extended or adjusted under 35 U.S.C. 154(b) by 315 days.

(21) Appl. No.: 16/246,518

(22) Filed: Jan. 13, 2019

(65) Prior Publication Data

US 2019/0143061 A1  May 16, 2019

Related U.S. Application Data

(63) Continuation of application No. PCT/CN2017/100880, filed on Sep. 7, 2017.

(30) Foreign Application Priority Data

Sep. 22, 2016  (CN) .......................... 201610839387.9

(51) Int. Cl.
*A61M 16/00* (2006.01)
*A61M 16/10* (2006.01)
(Continued)

(52) U.S. Cl.
CPC ...... *A61M 16/024* (2017.08); *A61M 16/0051* (2013.01); *A61M 16/0677* (2014.02);
(Continued)

(58) Field of Classification Search
CPC .............. A61M 16/00; A61M 16/0057; A61M 16/0066; A61M 16/0069; A61M 16/01;
(Continued)

(56) References Cited

U.S. PATENT DOCUMENTS

2007/0023039 A1* 2/2007 Ishizaki ................. G16H 20/13
128/201.21
2009/0107500 A1  4/2009 Edwards
(Continued)

FOREIGN PATENT DOCUMENTS

CN  203625036 U  6/2014
CN  203861719 U  10/2014
(Continued)

OTHER PUBLICATIONS

Machine translation of DE-102010035167-A1.*
Internation Search Report of PCT/CN2017/100880, dated Dec. 1, 2017.

*Primary Examiner* — Joseph D. Boecker

(57) ABSTRACT

An oxygen generator for respiration-synchronized oxygen supply is provided. An ultrasonic gas sensor is used in the oxygen generator to act as a detection element for detecting human inhalation or respiration. On the basis of data corresponding to the human inhalation detected by the ultrasonic gas sensor, a control unit makes an oxygen generating unit supply oxygen to a human body through an oxygen delivery pipeline only when the human body inhales, and not supply the oxygen to the human body at the rest of time, thereby realizing respiration-synchronized oxygen supply. The respiration-synchronized oxygen supply by the oxygen generator is realized at low cost with simple and convenient control, thereby greatly reducing the cost, volume, weight, energy consumption and noise of the oxygen generator and increasing portability.

4 Claims, 9 Drawing Sheets

(51) Int. Cl.
*A61M 16/06* (2006.01)
*A61M 16/20* (2006.01)
*A61B 5/00* (2006.01)
*A61B 5/08* (2006.01)

(52) U.S. Cl.
CPC ....... *A61M 16/1005* (2014.02); *A61B 5/0816* (2013.01); *A61B 5/4836* (2013.01); *A61M 16/0078* (2013.01); *A61M 16/202* (2014.02); *A61M 2016/0018* (2013.01); *A61M 2016/0039* (2013.01); *A61M 2016/1025* (2013.01); *A61M 2202/0208* (2013.01); *A61M 2205/18* (2013.01); *A61M 2205/3334* (2013.01); *A61M 2205/3375* (2013.01); *A61M 2205/50* (2013.01); *A61M 2205/70* (2013.01); *A61M 2230/42* (2013.01)

(58) Field of Classification Search
CPC .............. A61M 16/022; A61M 16/024; A61M 16/0677; A61M 16/08; A61M 16/0841; A61M 16/085; A61M 16/10; A61M 16/1005; A61M 16/101; A61M 16/1015; A61M 16/202; A61M 16/204; A61M 2016/0018; A61M 2016/0021; A61M 2016/0024; A61M 2016/0033; A61M 2016/0039; A61M 2016/1025; A61M 2202/0208; A61M 2230/42; A61M 2230/435; A61B 5/0833
See application file for complete search history.

(56) References Cited

U.S. PATENT DOCUMENTS

| | | | |
|---|---|---|---|
| 2010/0242734 A1* | 9/2010 | Maeda | A61M 16/10 96/110 |
| 2012/0055475 A1* | 3/2012 | Wilkinson | A61M 16/101 128/204.21 |
| 2016/0166787 A1 | 6/2016 | Morrison et al. | |

FOREIGN PATENT DOCUMENTS

| | | | |
|---|---|---|---|
| CN | 204468938 U | 7/2015 | |
| CN | 105377346 A | 3/2016 | |
| CN | 106215299 A | 12/2016 | |
| CN | 106267496 A | 1/2017 | |
| CN | 206566327 U | 10/2017 | |
| DE | 102010035167 A1 * | 2/2012 | ............ A61M 16/20 |
| JP | 2002065856 A | 3/2002 | |

* cited by examiner

OXYGEN GENERATOR FOR RESPIRATION-SYNCHRONIZED OXYGEN SUPPLY

CROSS-REFERENCE TO RELATED APPLICATIONS

This application is a continuation of International Patent Application No. PCT/CN2017/100880 with a filing date of Sep. 7, 2017, designating the United States, now pending, and further claims priority to Chinese Patent Application No. 201610839387.9 with a filing date of Sep. 22, 2016. The content of the aforementioned applications, including any intervening amendments thereto, are incorporated herein by reference.

TECHNICAL FIELD

The present disclosure relates to the field of oxygen generators capable of supplying oxygen.

BACKGROUND OF THE PRESENT INVENTION

The oxygen generator is a medical healthcare product, and can supply oxygen for people who need it. The oxygen generators used at present are mainly classified into the following two types according to oxygen supply modes:

The first type is an oxygen generator which can only continuously supply oxygen. This oxygen generator continuously delivers oxygen to a human body at a set flow during operation regardless of a respiration state of the human body. Even if the human body exhales and does not need the oxygen, the oxygen generator does not stop the delivery of oxygen. Therefore, the supplied oxygen is often wasted, and the utilization rate of the supplied oxygen is very low.

The second type is an oxygen generator which can conduct respiration-synchronized oxygen supply. This oxygen generator always detects the respiration state of the human body during operation, and delivers the oxygen to the human body only at the early stage of human inhalation, and does not output the oxygen at the rest of time. The utilization rate of the supplied oxygen of this oxygen generator is very high, and the oxygen is hardly wasted.

If the oxygen generators are classified according to human oxygen inhalation modes, there are two oxygen inhalation modes including an open oxygen inhalation mode in which nasal tubes or oxygen outlets are positioned near nostrils, and a sealed oxygen inhalation mode by wearing a mask. Considering the comfort, the open oxygen inhalation mode is generally used.

The oxygen generator which can supply the oxygen in the mode of respiration-synchronized oxygen supply supplies the oxygen to the human body only at the early stage of human inhalation, so that the oxygen supply required to achieve the same therapeutic effect is reduced to about ¼-⅙ of the oxygen supply required by the continuous oxygen supply mode for the following reasons:

Firstly, the inhalation and exhalation ratio of the human body is generally 1:1.5 to 1:2, i.e., inhalation time accounts only about 33%-40% of the total respiration cycle.

Secondly, the tidal volume of a normal human body is about 500 ml. The volume of a non-gas exchange part in a respiratory tract (such as trachea, etc.) of the human body is about 150 ml (the volume of this part is also known as a physiological invalid cavity). When the human body inhales, exhaust gas that stays in the respiratory tract at the time of exhaling in the last time enters pulmonary alveoli firstly. In about 500 ml of gas inhaled by the human body each time, only about 350 ml of gas enters the lung, and about 150 ml of gas stays in the respiratory tract. Namely, by taking 500 ml of moisture gas as an example, the ratio of the gas that enters the alveoli is about 70%.

Thirdly, in about 350 ml of gas that enters the pulmonary alveoli, the gas that enters at the last 0.3 second cannot complete gas exchange and is expelled from the lung, so the utilization rate of the gas is greatly reduced. Moreover, as the respiration cycle is shortened, the proportion of this gas will be increased greatly. The time of each inhalation is about 1-2 seconds through computation based on a respiration frequency of 12-20 times per minute and an inhalation and exhalation ratio of 1:1.5 to 1:2. In about 350 ml of gas that enters the alveoli, the part that can be fully used by the human body occupies a maximum of about 85% and a minimum of about 70%.

Fourthly, when the human body inhales atmosphere with an oxygen concentration of about 21%, it takes about 0.3 second for the human body to complete normal gas exchange. However, when the human body makes full use of high-concentration oxygen outputted by the oxygen generator with a mixed concentration of about 30%, a longer gas exchange time is needed. Therefore, in about 350 ml of gas that enters the alveoli, the part that can be fully used by the human body is lower than the above 70%-85%.

In combination with the above data, the utilization rate of the oxygen during continuous oxygen supply is at most 16.2%-23.8%, which is about ¼-⅙.

An oxygen generator widely used currently for supplying oxygen continuously includes: a control unit for controlling the operation of the oxygen generator, an oxygen generating unit, a flow adjusting device and an oxygen delivery pipeline for delivering oxygen supplied by the oxygen generating unit to the human body. The oxygen generating unit generally includes an oxygen producing unit for generating oxygen, a gas storage tank component for storing the oxygen, etc. The flow adjusting device is disposed on the oxygen delivery pipeline of the oxygen generator for continuously supplying oxygen; an oxygen concentration sensor for measuring an oxygen concentration may also be disposed; or a flow sensor for measuring an oxygen flow, and a humidification bottle for increasing oxygen humidity may also be disposed. During use, an outer end of the oxygen delivery pipeline is generally communicated to human nostrils. After the flow of high-pressure oxygen outputted by the oxygen generating unit is adjusted by the flow adjusting device, the oxygen is continuously supplied to the human body through the oxygen delivery pipeline. In this process, the oxygen concentration sensor and the flow sensor transmit the data of the detected oxygen concentration and the detected flow to the control unit, and the control unit processes the data. When the oxygen supply concentration is lower than a set value, the control unit has an alarm signal for alarm.

The above oxygen generator for continuously supplying oxygen has the advantage of simple control, and has the disadvantages as follows: (1) the oxygen generator is large in volume, heavy in weight, inconvenient in carrying, large in energy consumption and large in noise; furthermore, because the oxygen delivery pipeline still continuously outputs the oxygen when the human body exhales, in one aspect, user comfort is poor and in another aspect, the oxygen is seriously wasted; and (2) because the oxygen outputted by the oxygen generator is large and very dry, the humidification bottle needs to be equipped to humidify the outputted oxygen, which further increases the cost of the oxygen generator.

A currently used oxygen generator for respiration-synchronized oxygen supply includes: a control unit for controlling the operation of the oxygen generator, an oxygen generating unit, an oxygen supply unit for delivering the oxygen provided by the oxygen generating unit to the human body, and a detection element which is capable of detecting human respiration. The oxygen generating unit generally includes an oxygen producing unit for generating oxygen, a gas storage tank component for storing the oxygen, etc. The oxygen supply unit generally includes an oxygen delivery pipeline for delivery oxygen, an oxygen supply valve disposed on the oxygen delivery pipeline, an oxygen concentration sensor possibly disposed, etc. The detection element which is capable of detecting human respiration is a micro differential pressure sensor. During use, an outer end of the oxygen delivery pipeline is communicated to human nostrils. When the human body respires, the micro differential pressure sensor is capable of detecting a small differential pressure change between air pressure in the pipe in the micro differential pressure sensor and outside air pressure caused by human exhalation and inhalation. When the human body inhales, the air pressure in the pipe is slightly lower than the air pressure outside the pipe. When the human body exhales, the air pressure in the pipe is slightly higher than the air pressure outside the pipe. During operation, according to the small differential pressure data detected by the micro differential pressure sensor in human inhalation and exhalation, the oxygen supply valve is open only at the early stage of human inhalation, and is in a closed state at the rest of time. Namely, only when the human body inhales, the oxygen generating unit can supply the oxygen to the human body through the oxygen delivery pipeline, and cannot supply the oxygen to the human body through the oxygen delivery pipeline at the rest of time, thereby realizing an operation mode of respiration-synchronized oxygen supply. During operation, oxygen concentration data delivered by the oxygen concentration sensor are used as oxygen supply concentration of the oxygen generator at this moment. When the oxygen supply concentration is lower than a set value, the control unit has an alarm signal for alarm.

The existing respiration-synchronized oxygen supply technique is mainly applied to a portable oxygen generator with high selling price. It has the advantages of small volume, light weight, convenient carrying, low energy consumption and low noise, and has the disadvantages that an expensive micro differential pressure sensor needs to be equipped and the micro differential pressure detection technique has high difficulty. Due to high cost and high technical difficulty of the micro differential pressure sensor, the respiration-synchronized oxygen supply technique is only used in the expensive portable oxygen generator at present, and cannot be popularized to a larger number of cheaper desktop oxygen generators, so the application range is very narrow.

At present, an ultrasonic gas sensor based on an ultrasonic detection principle are used for measuring the size and the direction of the flow of the gas, and the content of each gas composition (also known as the concentration of each gas composition) in a gas mixture. This ultrasonic gas sensor has the advantages of low cost, high accuracy, long service life, good stability, rapid response, short detection period, individual or simultaneous measurement for gas concentration and size and direction of gas flow (i.e., bidirectional flow detection capability), etc. In practical application, when the ultrasonic gas sensor is only used for detecting the gas concentration, the ultrasonic gas sensor is generally called as an ultrasonic gas concentration sensor, and when the ultrasonic gas sensor is only used for detecting the gas flow, the ultrasonic gas sensor is generally called as an ultrasonic gas flowmeter. Generally, the ultrasonic gas sensor is capable of detecting both the gas concentration, and the gas flow and the flowing direction of the gas.

In conclusion, in the field of the oxygen generator, especially in the open oxygen inhalation mode, how to enable the oxygen generator to simply, conveniently and accurately realize respiration-synchronized oxygen supply at low cost is always a technical problem that exists and is explored in this field.

SUMMARY OF PRESENT INVENTION

The purpose of the present disclosure is to provide an oxygen generator for respiration-synchronized oxygen supply capable of greatly reducing the manufacturing cost, volume and weight of the oxygen generator and greatly reducing energy consumption and noise.

The present disclosure creatively uses a cheap ultrasonic gas sensor as a detection element in the oxygen generator, so that the oxygen generator can have the function of respiration-synchronized oxygen supply. Thus, under the condition of achieving the same oxygen inhalation effect, the manufacturing cost, volume and weight of the oxygen generator is greatly reduced, thereby reducing selling price. The oxygen generator is also convenient for carrying, and energy consumption and noise are also greatly reduced.

To achieve the above purpose, the present disclosure adopts the following technical solutions.

An oxygen generator for respiration-synchronized oxygen supply includes a control unit for controlling operation of the oxygen generator, an oxygen generating unit, an oxygen supply unit for delivering oxygen provided by the oxygen generating unit to a human body, a detection element for detecting human inhalation or respiration, and an airflow forming device; the oxygen supply unit includes an oxygen delivery pipeline which is capable of communicating with a human respiratory organ and an oxygen supply valve disposed on the oxygen delivery pipeline, an ultrasonic gas sensor is used as the detection element for detecting human inhalation or respiration; the airflow forming device is configured to form an airflow at least corresponding to the human inhalation in the ultrasonic gas sensor during human respiration, so that the ultrasonic gas sensor can detect at least the human inhalation; and during operation, according to data or signals corresponding to the human inhalation or respiration detected by the ultrasonic gas sensor, the oxygen supply unit is configured to supply oxygen to the human body through the oxygen delivery pipeline only when the human body inhales, and does not supply the oxygen to the human body at rest, thereby realizing respiration-synchronized oxygen supply.

Further, in the oxygen generator for respiration-synchronized oxygen supply, the ultrasonic gas sensor is capable of detecting both a human inhalation or respiration airflow and an oxygen concentration; and in this way, the ultrasonic gas sensor is configured to detect both the human inhalation or respiration airflow and the oxygen concentration of gas outputted by the oxygen generator.

Further, in the oxygen generator for respiration-synchronized oxygen supply, a bypass pipe is communicated to the oxygen delivery pipeline communicated to a gas outlet of the oxygen supply valve; an outer end of the bypass pipe is communicated with a first vent on the ultrasonic gas sensor, a second vent on the ultrasonic gas sensor is communicated with atmosphere; at a starting moment when the oxygen generator begins to operate, the oxygen supply valve is in a closed state; moreover, at least when the human body inhales, the bypass pipe ensures an inhalation airflow corresponding to the human inhalation is formed in the ultrasonic gas sensor, so that the ultrasonic gas sensor is capable of detecting both the human inhalation; and during operation, according to data or signals corresponding to the human inhalation detected by the ultrasonic gas sensor, the oxygen supply valve is open for a set time only when the human body inhales, and is in a closed state at rest, so that the oxygen supply unit supplies oxygen to the human body through the oxygen delivery pipeline only when the human body inhales.

More further, in the oxygen generator for respiration-synchronized oxygen supply, the second vent on the ultrasonic gas sensor is communicated with atmosphere through a section of pipeline; and in this way, when the oxygen supply valve is closed during operation once oxygen supply is finished, oxygen concentration data detected by the ultrasonic gas sensor at this moment are used as oxygen supply concentration data of the oxygen generator at this moment.

More further, in the oxygen generator for respiration-synchronized oxygen supply, a bypass control valve for controlling a communication time between the oxygen delivery pipeline and the atmosphere through the bypass pipe; the bypass control valve is disposed in the bypass pipe; at a starting moment when the oxygen generator begins to operate, the oxygen supply valve is in a closed state and meanwhile, the bypass control valve is in an open state; in this way, at an initial moment of startup, the bypass pipe ensures an inhalation airflow corresponding to the human inhalation is formed in the ultrasonic gas sensor, so that the ultrasonic gas sensor is capable of detecting both the human inhalation; and during operation, once the oxygen supply valve is open and ventilation is completed in the ultrasonic gas sensor, the bypass control valve is closed; and until the oxygen supply valve is closed after the oxygen supply is finished in current circle, the bypass control valve is open again, so that the bypass pipe ensures that the ultrasonic gas sensor accurately detects each human inhalation and oxygen waste is reduced. In addition, in practical operation, when the bypass control valve is closed, the ultrasonic gas sensor can be subjected to zero correction of flow. Moreover, during operation, once the bypass control valve is closed, oxygen concentration data detected by the ultrasonic gas sensor at this moment are used as oxygen supply concentration data of the oxygen generator at this moment.

More further, in the oxygen generator for respiration-synchronized oxygen supply, the second vent on the ultrasonic gas sensor is communicated with a gas storage chamber and is not communicated with atmosphere; and the gas storage chamber and the bypass pipe are configured to form an inhalation airflow at least corresponding to the human inhalation in the ultrasonic gas sensor, so that the ultrasonic gas sensor is capable of detecting the human inhalation. In practical manufacture, the gas storage chamber is a gas storage bag having a volume changing with internal gas pressure. When the gas storage bag is completely full or empty due to the human respiration, the ultrasonic gas sensor can be subjected to zero correction of flow. Moreover, during operation, when the oxygen supply valve is closed once oxygen supply is finished, oxygen concentration data detected by the ultrasonic gas sensor at this moment are used as oxygen supply concentration data of the oxygen generator at this moment.

Further, in the oxygen generator for respiration-synchronized oxygen supply, the ultrasonic gas sensor is disposed in the oxygen delivery pipeline communicated to the gas outlet of the oxygen supply valve; the bypass pipe is communicated to the oxygen delivery pipeline communicated between the gas outlet of the oxygen supply valve and the ultrasonic gas sensor, the outer end of the bypass pipe is communicated with atmosphere; at a starting moment when the oxygen generator begins to operate, the oxygen supply valve is in a closed state; moreover, at least when the human body inhales, the bypass pipe ensures an inhalation airflow corresponding to the human inhalation is formed in the ultrasonic gas sensor, so that the ultrasonic gas sensor is capable of detecting the human inhalation; and during operation, according to data or signals corresponding to the human inhalation detected by the ultrasonic gas sensor, the oxygen supply valve is open for a set time only when the human body inhales, and is in a closed state at rest, so that the oxygen supply unit supplies oxygen to the human body through the oxygen delivery pipeline only when the human body inhales.

More further, in the oxygen generator for respiration-synchronized oxygen supply, during operation, when the oxygen supply valve is closed once oxygen supply is finished, oxygen concentration data detected by the ultrasonic gas sensor at this moment are used as oxygen supply concentration data of the oxygen generator at this moment.

More further, in the oxygen generator for respiration-synchronized oxygen supply, the bypass control valve is disposed in the bypass pipe; at a starting moment when the oxygen generator begins to operate, the oxygen supply valve is in a closed state; and meanwhile, the bypass control valve is in an open state; in this way, at an initial moment of startup, the bypass pipe ensures an inhalation airflow corresponding to the human inhalation is formed in the ultrasonic gas sensor, so that the ultrasonic gas sensor is capable of detecting the human inhalation; and during operation, once the oxygen supply valve is open, the bypass control valve is closed; and until the oxygen supply valve is closed after the oxygen supply is finished in current circle, the bypass control valve is open again, so that the bypass pipe ensures that the ultrasonic gas sensor accurately detects each human inhalation. Moreover, when the bypass control valve is closed, the ultrasonic gas sensor can be subjected to zero correction of flow. During operation, when the oxygen supply valve is closed once oxygen supply is finished, oxygen concentration data detected by the ultrasonic gas sensor at this moment are used as oxygen supply concentration data of the oxygen generator at this moment; and after the detection of the oxygen concentration is completed, the bypass control valve is open, so that the bypass pipe ensures that the ultrasonic gas sensor accurately detects each human inhalation.

More further, in the oxygen generator for respiration-synchronized oxygen supply, the outer end of the bypass pipe is connected with a gas storage chamber and is not communicated with atmosphere; and the gas storage chamber and the bypass pipe are configured to form an inhalation airflow at least corresponding to the human inhalation in the ultrasonic gas sensor, so that the ultrasonic gas sensor is capable of detecting the human inhalation. In practical manufacture, the gas storage chamber is a gas storage bag having a volume changing with internal gas pressure. When the gas storage bag is completely full or empty due to the human respiration, the flow in the ultrasonic gas sensor is zero and air pressure is close to the outside atmospheric pressure, then the ultrasonic gas sensor can be subjected to zero correction of flow. Moreover, during operation, when the oxygen supply valve is closed once oxygen supply is finished, oxygen concentration data detected by the ultrasonic gas sensor at this moment are used as oxygen supply concentration data of the oxygen generator at this moment.

The oxygen generator provided in present disclosure has the beneficial effects: compared with a currently launched oxygen generator for respiration-synchronized oxygen supply for detecting the human respiration using a differential pressure sensor, the present oxygen generator uses an ultrasonic gas sensor with cheap price and simple and convenient detection technique as a detection element for respiration in the oxygen generator, so that the detection for respiration is realized at low cost and respiration-synchronized oxygen supply is realized, thereby greatly reducing the manufacturing cost of the oxygen generator for respiration-synchronized oxygen supply. Moreover, the ultrasonic gas sensor which is capable of detecting both a gas flow and an oxygen concentration can be adopted, thereby further saving the expense of an oxygen concentration sensor and further reducing the cost of the oxygen generator. The present disclosure can popularize a respiration-synchronized oxygen supply technique from an expensive portable oxygen generator to a larger number of cheaper desktop oxygen generators, so that the oxygen generator for respiration-synchronized oxygen supply becomes a medical healthcare product that is affordable for the general public.

DETAILED DESCRIPTION OF PREFERRED EMBODIMENTS

The present disclosure is further described below in combination with drawings and preferred embodiments, but the present disclosure is not only limited to these embodiments.

Figure 1:
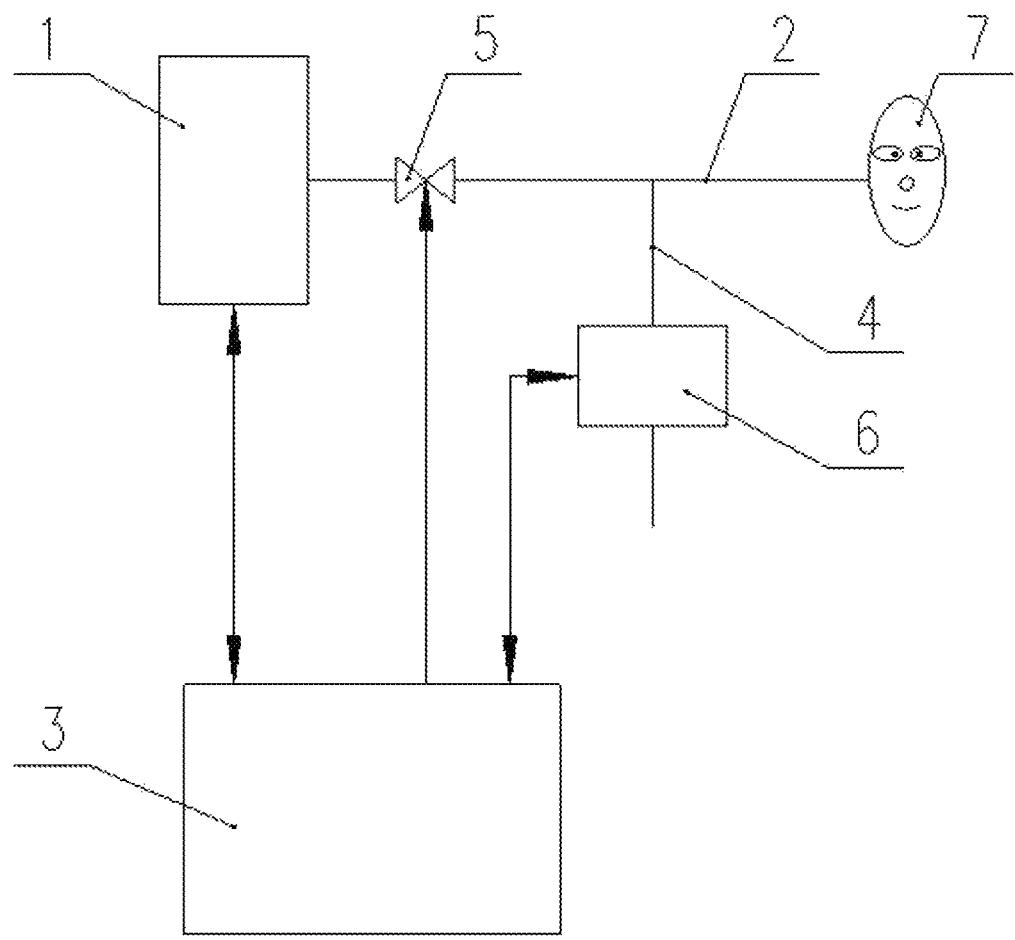
FIG. 1 is a structural schematic diagram of an oxygen generator according to a first embodiment of the present disclosure.

FIG. 1 shows a first embodiment of an oxygen generator for respiration-synchronized oxygen supply in the present disclosure. The oxygen generator for respiration-synchronized oxygen supply includes a control unit 3 for controlling the normal operation of the oxygen generator, an oxygen generating unit 1 and an oxygen supply unit for delivering oxygen provided by the oxygen generating unit 1 to a human body. The oxygen supply unit includes an oxygen delivery pipeline 2 which is capable of communicating with a human respiratory organ and an oxygen supply valve 5 disposed in the oxygen delivery pipeline 2. The oxygen generator also includes a detection element which is capable of detecting human inhalation or respiration. In the present disclosure, an ultrasonic gas sensor 6 is used as a detection element for detecting human inhalation or respiration. The control unit 3 can transmit data or signals to the ultrasonic gas sensor 6 and can also receive date or signals therefrom. An airflow forming device is also disposed in the oxygen generator. When the human body respires, the airflow forming device is configured to form an airflow at least corresponding to the human inhalation in the ultrasonic gas sensor 6, so that the ultrasonic gas sensor 6 can at least detect the human inhalation. During operation, according to data or signals corresponding to the human inhalation or respiration detected by the ultrasonic gas sensor 6, the oxygen supply unit supplies oxygen to the human body through the oxygen delivery pipeline 2 only when the human body inhales, and does not supply the oxygen to the human body at the rest of time, thereby realizing respiration-synchronized oxygen supply. In the present embodiment, a bypass pipe 4 is communicated to the oxygen delivery pipeline 2 which is communicated to a gas outlet of the oxygen supply valve 5. An outer end of the bypass pipe 4 is communicated with a first vent on the ultrasonic gas sensor 6. A second vent on the ultrasonic gas sensor 6 is communicated with atmosphere. During use, an outer end of the oxygen delivery pipeline 2 is communicated to nostrils of the human body 7. The bypass pipe 4 and part of the oxygen delivery pipeline between the bypass pipe and the human respiratory organ form the airflow forming device. At a starting moment when the oxygen generator begins to operate, the oxygen supply valve 5 is in a closed state. When the human body respires, the airflow forming device including the bypass pipe 4 is capable of forming an inhalation airflow corresponding to human inhalation and forming an exhalation airflow corresponding to human exhalation in the ultrasonic gas sensor 6, so that the ultrasonic gas sensor 6 is capable of detecting each human inhalation as the detection element for respiration, and certainly capable of detecting the initial moment of each human inhalation. During operation, according to data corresponding to human inhalation or the initial inhalation moment detected by the ultrasonic gas sensor 6, the oxygen supply valve 5 is open for a set time only when the human body inhales each time, and is in a closed state at the rest of time, so that the oxygen supply unit supplies a set amount of oxygen to the human body through the oxygen delivery pipeline 2 only when the human body inhales each time. In practical operation, the oxygen supply unit can supply the oxygen to the human body through the oxygen delivery pipeline 2 only in the early stage of each human inhalation. For example, in a practical use process, the oxygen supply valve 5 can be controlled to open at any moment in 0.01 to 0.1 second after the human body begins to inhale each time, and is kept for a required time. The keeping time can be set by the actually required oxygen supply amount. The oxygen supply valve 5 is in a closed state at the rest of time. Oxygen supply at the early stage of human inhalation can enable the supplied oxygen to enter alveoli as early as possible to fully complete gas change, so as to ensure to satisfy the oxygen supply amount required by each human respiration and minimize ineffective oxygen supply amount of the oxygen generator, thereby greatly increasing the utilization rate of the oxygen supplied by the oxygen generator and increasing the operation efficiency of the oxygen generator.

In the present embodiment, the ultrasonic gas sensor 6 can also be an ultrasonic gas sensor which is capable of detecting both a human inhalation or respiration airflow and an oxygen concentration. Moreover, in practical operation, the second vent on the ultrasonic gas sensor is communicated with atmosphere through a section of pipeline. In this way, when the oxygen supply valve 5 completes each oxygen supply and is closed during operation, the ultrasonic gas sensor 6 is full of high-concentration oxygen released at this time. At this moment, the control unit 3 can use oxygen concentration data detected by the ultrasonic gas sensor 6 as real-time oxygen supply concentration data of the oxygen generator. When the oxygen supply concentration is lower than a set value, the control unit 3 has an alarm signal for alarm.

In the first embodiment, when the oxygen supply valve 5 is open, the delivered oxygen is not only delivered into the human body through the oxygen delivery pipeline 2, but also leaked into the atmosphere through the bypass pipe 4, causing oxygen waste. Therefore, the leakage amount of the bypass pipe 4 is limited through a technical means so that generated leakage can only ensure update of the gas in the ultrasonic gas sensor 6. Meanwhile, this technical means does not hinder normal detection of the ultrasonic gas sensor 6 for human respiration airflow. A simplest technical means is to reduce the inner diameter of the bypass pipe so that the oxygen amount leaked from the bypass pipe during oxygen supply is much smaller than the oxygen amount delivered to the human body through the oxygen delivery pipeline, but shall simultaneously ensure that the reduced inner diameter of the bypass pipe does not hinder the detection of the ultrasonic gas sensor for the human respiration airflow.

Figure 2:
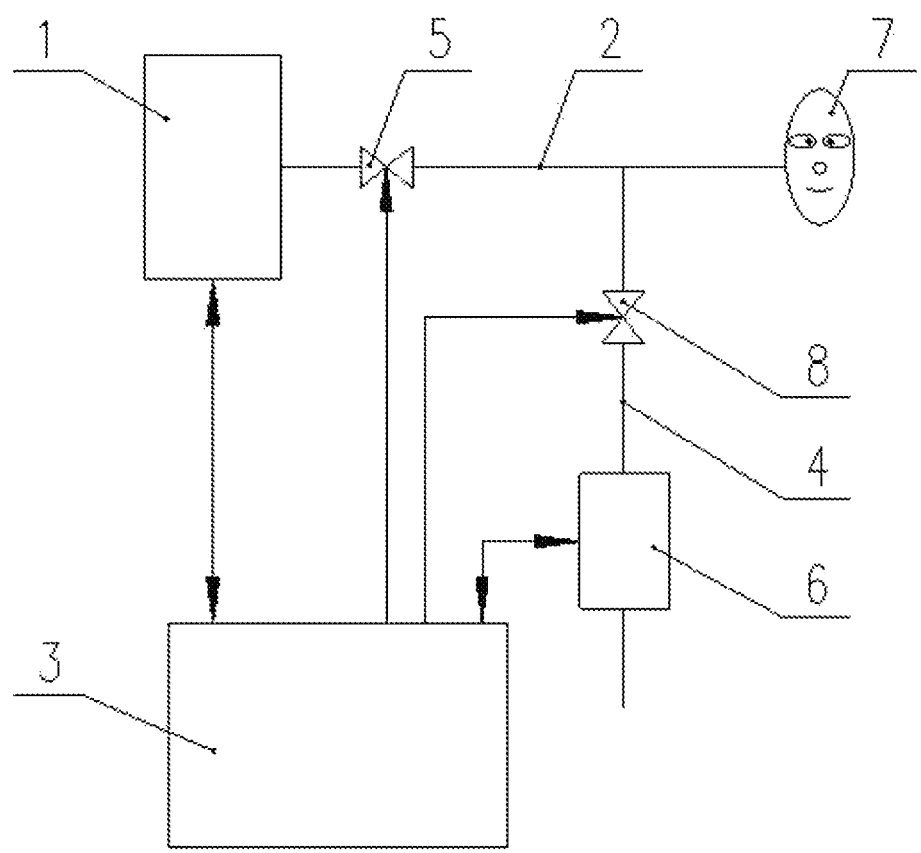
FIG. 2 is a structural schematic diagram of an oxygen generator according to a second embodiment of the present disclosure.

FIG. 2 shows a second embodiment of an oxygen generator for respiration-synchronized oxygen supply in the present invention. The oxygen generator for respiration-synchronized oxygen supply can overcome the disadvantage of waste of a large amount of oxygen in the first embodiment. It can be seen from FIG. 2 that, the second embodiment is different from the first embodiment shown in FIG. 1 in that: a bypass control valve 8 for controlling the communication time between the oxygen delivery pipeline 2 and atmosphere through the bypass pipe 4 is arranged. The bypass control valve 8 in the present embodiment is disposed in the bypass pipe 4. In the present embodiment, the bypass control valve 8, the bypass pipe 4 and part of the oxygen delivery pipeline between the bypass pipe 4 and a human respiratory organ form an airflow forming device. An operation control flow for realizing respiration-synchronized oxygen supply in the second embodiment is different from that in the first embodiment in that: at a starting moment when the oxygen generator begins to operate, the oxygen supply valve 5 is in a closed state and meanwhile, the bypass control valve 8 is in an open state. In this way, at an initial moment of startup, the airflow forming device including the bypass pipe 4 enables the ultrasonic gas sensor 6 to serve as a detection element for respiration to at least detect each human inhalation or the initial moment of each inhalation. During operation, once the oxygen supply valve 5 is open and ventilation is completed in the ultrasonic gas sensor 6, the bypass control valve 8 is closed; and until the oxygen supply valve 5 is closed after the oxygen supply is finished in current circle, the bypass control valve 8 is open again, so that the bypass pipe ensures that the ultrasonic gas sensor accurately detects each human inhalation and oxygen waste is reduced. Moreover, in practical operation, the ultrasonic gas sensor can be subjected to zero correction of flow when the bypass control valve 8 is closed and the flow in the ultrasonic gas sensor is zero, namely, when the air pressure in the bypass pipe 4 is close to the outside atmospheric pressure.

In addition, in the present embodiment, when the bypass control valve 8 is closed each time during operation, the control unit 3 can use oxygen concentration data detected by the ultrasonic gas sensor 6 as oxygen supply concentration data of the oxygen generator at this moment. When the oxygen supply concentration is lower than a set value, the control unit 3 has an alarm signal for alarm.

Figure 3:
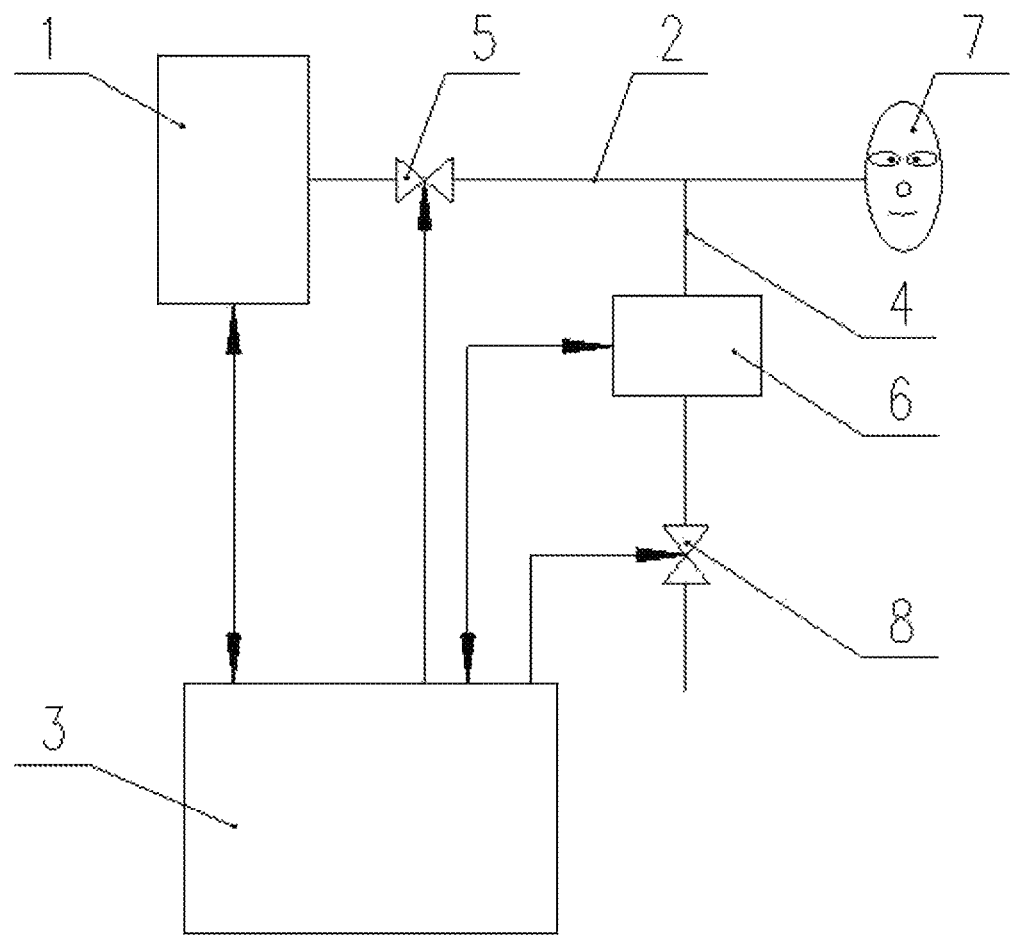
FIG. 3 is a structural schematic diagram of an oxygen generator according to a third embodiment of the present disclosure.

FIG. 3 shows a third embodiment of an oxygen generator for respiration-synchronized oxygen supply in the present invention. The oxygen generator for respiration-synchronized oxygen supply can also overcome the disadvantage of waste of a large amount of oxygen in the first embodiment. It can be seen from FIG. 3 that, the third embodiment is different from the first embodiment shown in FIG. 1 in that: the second vent on the ultrasonic gas sensor is connected with a section of external pipeline with the bypass control valve 8. In the present embodiment, the external pipeline, the bypass control valve 8, the bypass pipe 4 and part of the oxygen delivery pipeline between the bypass pipe 4 and a human respiratory organ form an airflow forming device.

The operation control flow for realizing respiration-synchronized oxygen supply in the third embodiment is the same as that in the second embodiment. In the aspect of detection of the oxygen supply concentration, the third embodiment is different from the second embodiment in that: when the oxygen supply valve 5 is closed each time during operation and the bypass control valve 8 is just open, the control unit 3 can use oxygen concentration data detected by the ultrasonic gas sensor 6 at this moment as oxygen supply concentration data of the oxygen generator at this moment. When the oxygen supply concentration is lower than a set value, the control unit 3 has an alarm signal for alarm.

In addition, in practical operation, the ultrasonic gas sensor can be subjected to zero correction of flow when the bypass control valve 8 is closed and the flow in the ultrasonic gas sensor is zero, namely, when the air pressure in the bypass pipe 4 is close to the outside atmospheric pressure.

The arrangement of the bypass control valve 8 in the above second embodiment and the third embodiment plays the roles: (1) the bypass control valve 8 is closed shortly after the oxygen supply valve 5 is open to limit the amount of the oxygen leaked from the bypass pipe 4, so that the amount of the oxygen leaked from the bypass pipe 4 is only enough to complete the update of the gas in the ultrasonic gas sensor 6; and (2) when the bypass control valve 8 is closed, the gas flow in the bypass pipe 4 is zero; and when the air pressure in the bypass pipe 4 is close to the outside atmospheric pressure, the ultrasonic gas sensor 6 can be subjected to zero correction of flow, so as to eliminate inevitable flow zero drift after long-term use.

Figure 4:
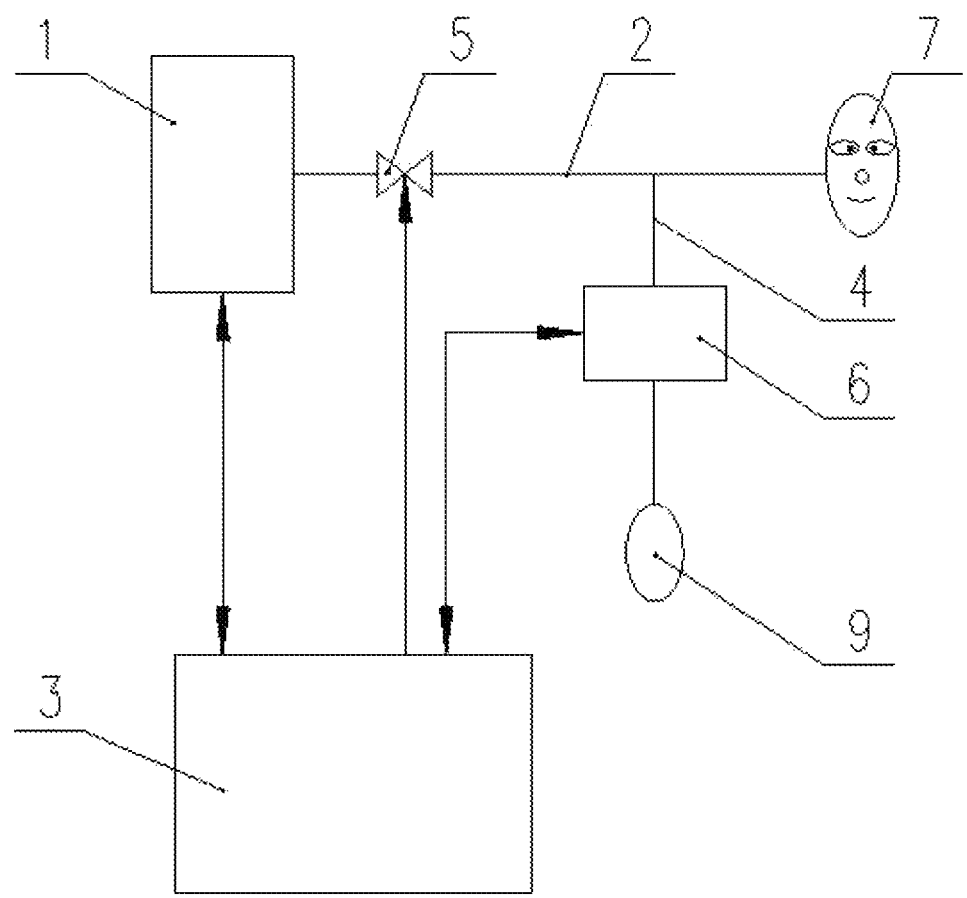
FIG. 4 is a structural schematic diagram of an oxygen generator according to a fourth embodiment of the present disclosure.

FIG. 4 shows a fourth embodiment of an oxygen generator for respiration-synchronized oxygen supply in the present invention. The oxygen generator for respiration-synchronized oxygen supply can also overcome the disadvantage of waste of a large amount of oxygen in the first embodiment. It can be seen from FIG. 4 that, the fourth embodiment is different from the first embodiment shown in FIG. 1 in that: the second vent on the ultrasonic gas sensor 6 is connected with a gas storage chamber 9 and is not communicated with atmosphere. In the present embodiment, the gas storage chamber is a gas storage bag 9 having a volume changing with the minor change of internal gas pressure. In the present embodiment, the gas storage bag 9, the bypass pipe 4 and part of the oxygen delivery pipeline between the bypass pipe 4 and the human respiratory organ form the airflow forming device. The airflow forming device including the gas storage bag 9 and the bypass pipe 4 are configured to form an inhalation airflow at least corresponding to human inhalation in the ultrasonic gas sensor 6, so that the ultrasonic gas sensor 6 can serve as a detection element for respiration to detect each human inhalation or the initial moment of each inhalation.

The greatest advantage of this mode is that the leakage of oxygen is prevented and the utilization rate of the oxygen supplied by the oxygen generator is increased. Meanwhile, the cost is almost not increased. The disadvantage of this mode is that the real-time performance of detection of the oxygen concentration is slightly reduced.

The operation control flow for realizing respiration-synchronized oxygen supply in the fourth embodiment is the same as that in the first embodiment. However, in the aspects of detection of the oxygen supply concentration and zero correction of flow, the fourth embodiment is different from the first embodiment in that: when the oxygen supply valve 5 completes each oxygen supply and is closed during operation, part of the gas in the gas storage bag 9 is inhaled out through the human inhalation airflow. When the human body completes inhalation and begins to exhale, the gas in the oxygen delivery pipeline 2 enters the gas storage bag 9 and the ultrasonic gas sensor 6. Such process is continuously repeated, and the gas in the gas storage bag 9 and the ultrasonic gas sensor 6 is gradually updated into the oxygen delivered out by the oxygen delivery pipeline. When the oxygen supply valve 5 completes each oxygen supply and is closed, the control unit 3 uses oxygen concentration data detected by the ultrasonic gas sensor 6 at this moment as oxygen supply concentration data of the oxygen generator at this moment. When the oxygen supply concentration is lower than a set value, the control unit 3 has an alarm signal for alarm. In addition, when the gas storage bag 9 is completely full or empty due to the human respiration, the flow in the ultrasonic gas sensor 6 may be zero for a short time, and the ultrasonic gas sensor 6 can be subjected to zero correction of flow through this characteristic.

In practical production, a proper material for making the gas storage bag 9 can be selected, so that the human respiration airflow is enough to make the gas storage bag 9 full or empty. A proper volume of the gas storage bag 9 can also be selected, so that a corresponding airflow can be formed in the ultrasonic gas sensor 6 at least at an initial moment when the human body completes exhalation and begins to inhale.

Figure 5:
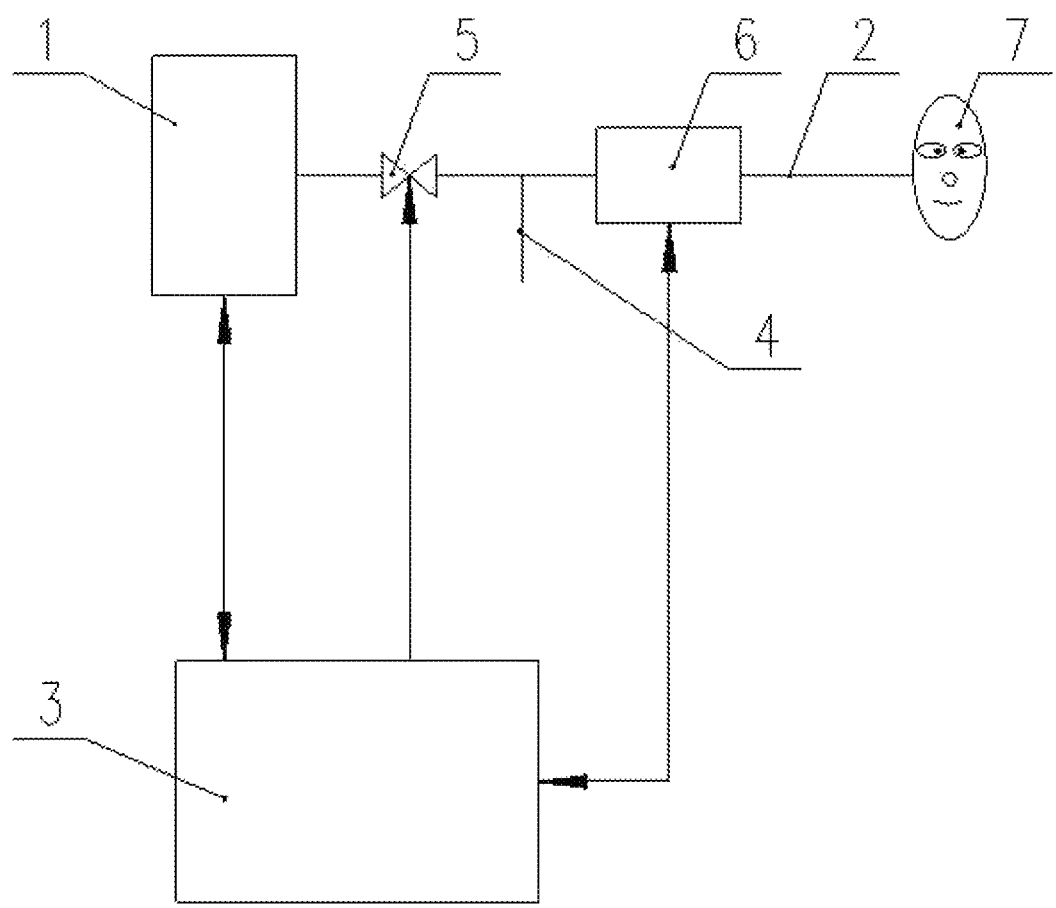
FIG. 5 is a structural schematic diagram of an oxygen generator according to a fifth embodiment of the present disclosure.

FIG. 5 shows a fifth embodiment of an oxygen generator for respiration-synchronized oxygen supply in the present invention. It can be seen from FIG. 5 that, the fifth embodiment is different from the first embodiment shown in FIG. 1 in that: the ultrasonic gas sensor 6 is disposed in the oxygen delivery pipeline 2 communicated to the gas outlet of the oxygen supply valve, while the bypass pipe 4 is communicated to the oxygen delivery pipeline 2 between the gas outlet of the oxygen supply valve 5 and the ultrasonic gas sensor 6, and the outer end of the bypass pipe 4 is communicated to the atmosphere. In the present embodiment, the bypass pipe 4 and part of the oxygen delivery pipeline between the bypass pipe 4 and the human respiratory organ form the airflow forming device.

The operation control flow for realizing respiration-synchronized oxygen supply in the fifth embodiment is the same as that in the first embodiment. But the fifth embodiment has the following disadvantages: (1), the bypass pipe 4 may cause oxygen leakage and result in waste; (2) the ultrasonic gas sensor 6 disposed in the oxygen delivery pipeline 2 may be repeatedly impacted by large-flow oxygen supply airflows, which may cause poor effect on the life and the performance of the sensor, and (3) the ultrasonic gas sensor always has human respiration airflows or oxygen supply airflows, causing that zero correction of flow cannot be open.

In the present embodiment, when the oxygen supply valve is closed during operation once oxygen supply is finished, the control unit 3 uses oxygen concentration data detected by the ultrasonic gas sensor 6 at this moment as oxygen supply concentration data of the oxygen generator at this moment.

Figure 6:
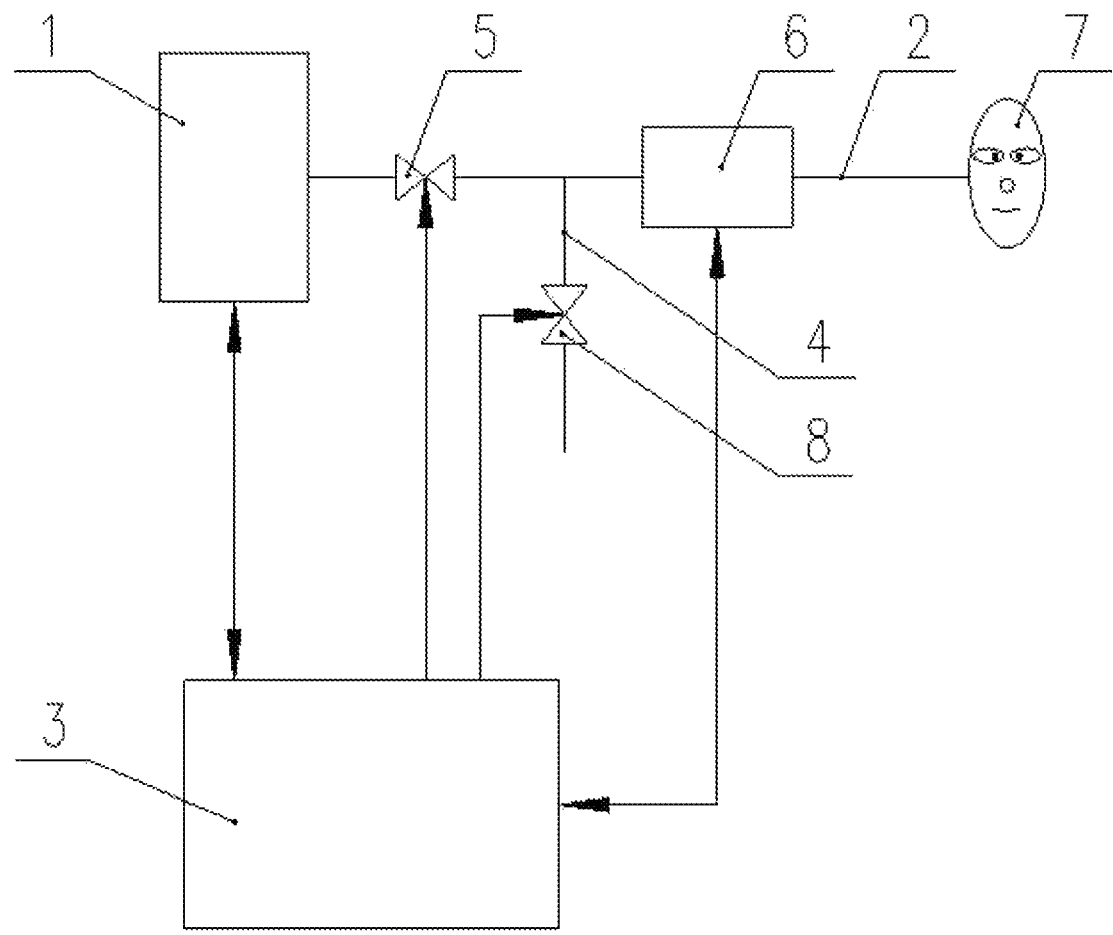
FIG. 6 is a structural schematic diagram of an oxygen generator according to a sixth embodiment of the present disclosure.

FIG. 6 shows a sixth embodiment of an oxygen generator for respiration-synchronized oxygen supply in the present invention. It can be seen from FIG. 6 that, the sixth embodiment is different from the fifth embodiment shown in FIG. 5 in that: the bypass control valve 8 is disposed in the bypass pipe 4. In the present embodiment, the bypass control valve 8, the bypass pipe 4 and part of the oxygen delivery pipeline between the bypass pipe 4 and the human respiratory organ form the airflow forming device. The sixth embodiment can greatly reduce the leakage amount of the oxygen.

The operation control flow for realizing respiration-synchronized oxygen supply in the sixth embodiment is different from that in the second embodiment in that: during operation, once the oxygen supply valve 5 is open, the bypass control valve 8 is closed; and until the oxygen supply valve 5 is closed after the oxygen supply is finished in current circle, the bypass control valve 8 is open again, so that the bypass pipe 4 ensures that the ultrasonic gas sensor 6 accurately detects each human inhalation and can also further reduce oxygen waste.

In addition, when the oxygen supply valve 5 completes each oxygen supply and is closed, the control unit 3 uses oxygen concentration data detected by the ultrasonic gas sensor 6 as oxygen supply concentration data of the oxygen generator at this moment, thereby realizing the function of detecting the oxygen supply concentration. Then, the control unit 3 controls to conduct the bypass control valve 8, so that the bypass pipe 4 ensures that the ultrasonic gas sensor 6 accurately detects each human inhalation. When the oxygen supply concentration is lower than a set value, the control unit 3 has an alarm signal for alarm. In practical operation, when the oxygen supply valve 5 and the bypass control valve 8 are closed and the flow in the ultrasonic gas sensor 6 is zero, the control unit 3 can also perform zero correction of flow for the ultrasonic gas sensor 6.

Figure 7:
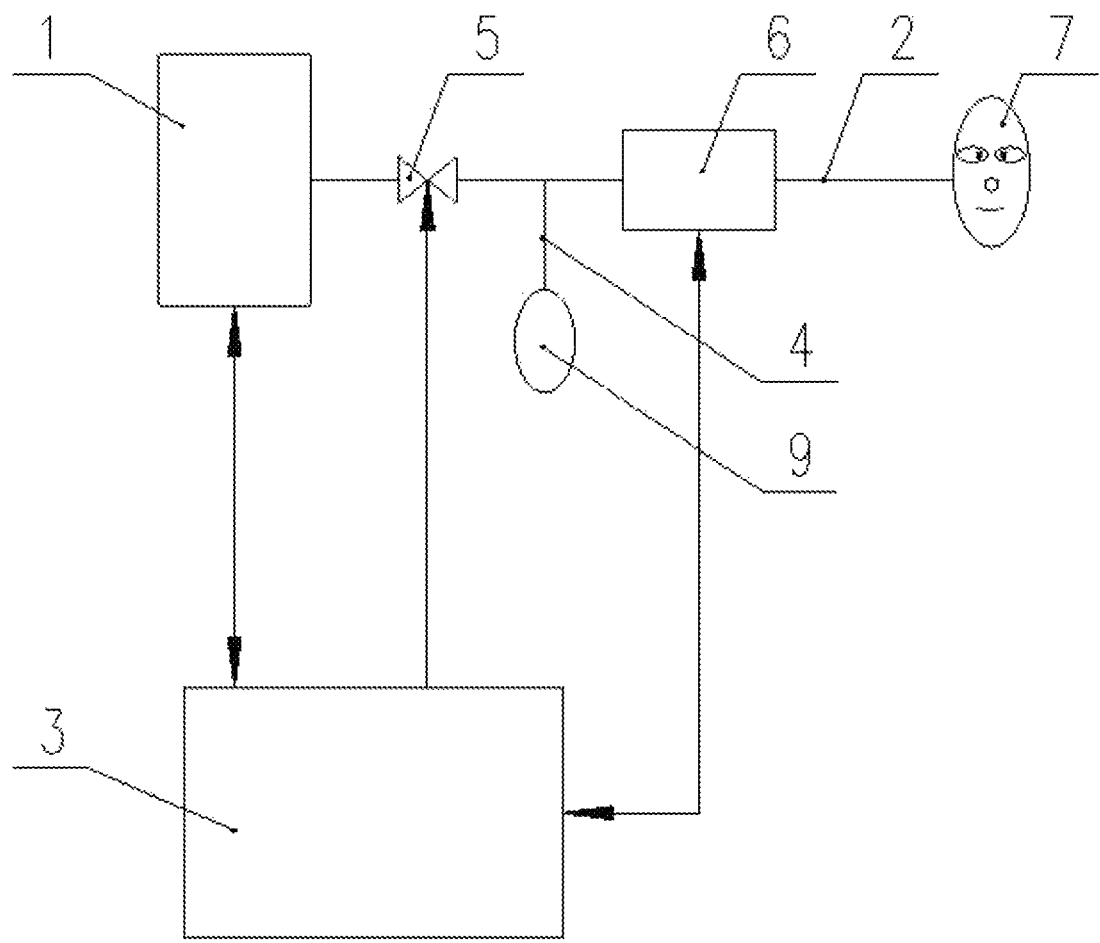
FIG. 7 is a structural schematic diagram of an oxygen generator according to a seventh embodiment of the present disclosure.

FIG. 7 shows a seventh embodiment of an oxygen generator for respiration-synchronized oxygen supply in the present invention. It can be seen from FIG. 7 that, the seventh embodiment is different from the fifth embodiment shown in FIG. 5 in that: an outer end of the bypass pipe 4 is connected with a gas storage chamber 9 and is not communicated with atmosphere. In the present embodiment, the gas storage chamber is a gas storage bag 9 having a volume changing with the minor change of internal gas pressure. In the present embodiment, the gas storage bag 9, the bypass pipe 4 and part of the oxygen delivery pipeline between the bypass pipe 4 and the human respiratory organ form the airflow forming device. The airflow forming device including the gas storage bag 9 and the bypass pipe 4 are configured to form an inhalation airflow at least corresponding to human inhalation in the ultrasonic gas sensor 6, so that the ultrasonic gas sensor 6 can serve as a detection element for respiration to detect each human inhalation or the initial moment of each inhalation.

The ultrasonic gas sensor can be subjected to zero correction of flow when the gas storage bag is completely full or empty due to the human respiration and the flow in the ultrasonic gas sensor is zero, namely, when the air pressure in the gas chamber pipeline in the ultrasonic gas sensor is close to the outside atmospheric pressure.

Compared with the fifth embodiment, the seventh embodiment increases almost no cost, and also avoids oxygen leakage, but has the disadvantage of reducing the real-time performance of detection of the oxygen supply concentration.

The operation control flow for realizing respiration-synchronized oxygen supply in the seventh embodiment is the same as that in the fifth embodiment shown in FIG. 5, and is not repeated herein.

In the above embodiments, an air filter can also be disposed on the bypass pipe or in the vent communicated with the atmosphere on the ultrasonic gas sensor, so as to avoid affecting the detection accuracy caused by that dust in the outside air is inhaled into the ultrasonic gas sensor.

In addition, in practical operation, the oxygen supply valve or the bypass control valve can be controlled by the control unit, and can also be controlled by the ultrasonic gas sensor. For example, the control unit computes the starting time of the oxygen supply valve according to the flow and the air pressure set by a user, and then the oxygen supply valve is started for the set time when the ultrasonic gas sensor detects human inhalation. Or, the control unit computes the starting time of the oxygen supply valve according to the flow and the air pressure set by the user and then sends the starting time to the ultrasonic gas sensor, the ultrasonic gas sensor starts the oxygen supply valve for the set time according to the data when ultrasonic gas sensor detects human inhalation. Or, the control unit sends the flow and the air pressure set by the user to the ultrasonic gas sensor, the ultrasonic gas sensor computes the starting time of the oxygen supply valve according to the data; and then, the oxygen supply valve is started for the set time when ultrasonic gas sensor detects human inhalation. Of course, the oxygen supply valve or the bypass control valve is not only limited to the above control mode. Technical solutions formed by adopting equivalent replacement or equivalent transformation shall belong to the protection scope claimed in the present invention.

Figure 8:
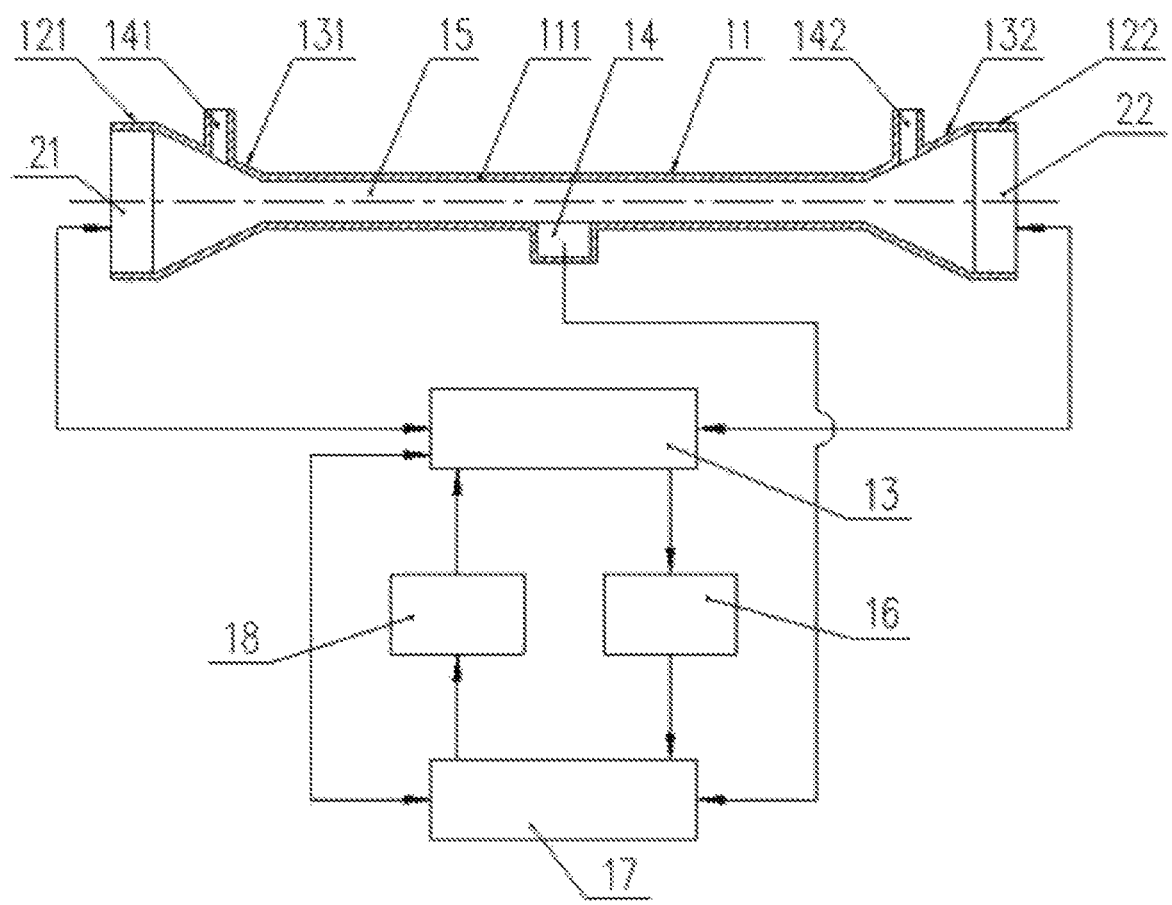
FIG. 8 is a structural schematic diagram of an ultrasonic gas sensor adopted in the present disclosure.
Figure 9:
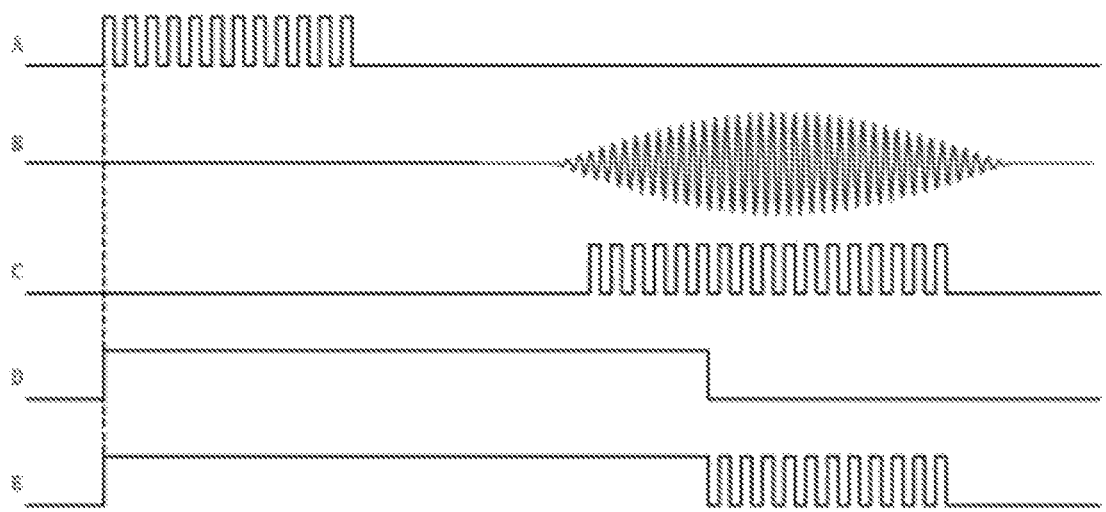
FIG. 9 is a schematic diagram of a signal waveform involved in the ultrasonic gas sensor shown in FIG. 8.

FIG. 8 is a structural schematic diagram of an ultrasonic gas sensor selected in the present invention. The structure specifically includes a closed gas chamber 15 used for accommodating to-be-detected gas. The gas chamber 15 includes a hollow pipe 11 with two closed ends. Vents are respectively disposed on side walls close to both ends of the hollow pipe 11, i.e., a first vent 141 and a second vent 142. In practical operation, the to-be-detected gas can enter the gas chamber 15 from the first vent 141 as needed, and can flow out of the gas chamber 15 from the second vent 142. Similarly, the to-be-detected gas can also enter the gas chamber 15 from the second vent 142, and can flow out of the gas chamber 15 from the first vent 141. A first ultrasonic transducer 21 and a second ultrasonic transducer 22 are respectively installed on both ends of the gas chamber 15 at set distances. Large pipe diameter segments are respectively formed on both ends of the hollow pipe 11 for installing the ultrasonic transducers. Namely, the left end of the hollow pipe 11 is provided with a left large pipe diameter segment 121 for installing the first ultrasonic transducer 21, and the right end is provided with a right large pipe diameter segment 122 for installing the second ultrasonic transducer 22. The pipe diameter of the middle part of the hollow pipe 11 is smaller than the large pipe diameter segments on both ends and forms a small pipe diameter segment 111. The gas chamber 15 also includes a gas measurement control system. The gas measurement control system includes: a transfer switch network 13 connected to the first ultrasonic transducer 21 and the second ultrasonic transducer 22 and capable of selectively exciting one ultrasonic transducer to emit ultrasonic waves and other ultrasonic transducer to receive the ultrasonic waves, a microprocessor 17 connected to the transfer switch network 13, a transmitting circuit 18 connected to the transfer switch network 13 and the microprocessor 17, and a receiving processing circuit 16. The microprocessor 17 excites the first ultrasonic transducer 21 to emit a first sound wave of multiple pulses at a given frequency through the transmitting circuit 18 and the transfer switch network 13. The first sound wave penetrates through the to-be-detected gas in the gas chamber 15, and forms a standing wave in the gas chamber 15. The second ultrasonic transducer 22 receives a first sound wave signal. The time from transmission to reception of the first sound wave is a first propagation time. Then, after the first sound wave disappears in the gas chamber 15 through damped oscillation, the microprocessor 17 excites the second ultrasonic transducer 22 to emit a second sound wave with the same frequency and the same pulse number as the first sound wave through the transmitting circuit 18 and the transfer switch network 13. The second sound wave penetrates through the to-be-detected gas in the gas chamber 15, and forms a standing wave in the gas chamber 15. The first ultrasonic transducer 21 receives a second sound wave signal. The time from transmission to reception of the second sound wave is a second propagation time. The microprocessor 17 measures and calculates the flow of the gas and/or the content of each gas composition in the to-be-detected gas according to the first propagation time and the second propagation time. The equivalent cross-sectional area of the pipeline between the first ultrasonic transducer 21 and the second ultrasonic transducer 22 is not greater than a quarter of the area of a circle that takes the wavelength of the first sound wave as a diameter. Moreover, when the cross-sectional area of the small pipe diameter segment is not greater than a quarter of the area of a transmitting end of the ultrasonic transducer, the large pipe diameter segments on both ends of the hollow pipe smoothly transit to the small pipe diameter segment in the middle of the hollow pipe respectively through horn bodies, i.e., the left large pipe diameter segment 121 smoothly transits to the left end of the small pipe diameter segment 111 of the hollow pipe through a left horn body 131, and the right large pipe diameter segment 122 smoothly transits to the right end of the small pipe diameter segment 111 of the hollow pipe through a right horn body 132. Moreover, two vents are respectively formed in two horn bodies of the hollow pipe. In the present embodiment, the first vent 141 is formed in the left horn body 131, and the second vent 142 is formed in the right horn body 132. A driving pulse of the above first sound wave and the second sound wave is shown by A waveform in FIG. 9. An envelope waveform of the above standing signal is shown by B waveform in FIG. 9. In the present embodiment, the left large pipe diameter segment 121, the right large pipe diameter segment 122 and the small pipe diameter segment 111 are in the shape of a cylinder, and the horn bodies are in the shape of a cone, i.e., the left horn body 131 and the right horn body 132 are in the shape of the cone.

The equivalent cross-sectional area of the pipeline means that: it is assumed that two ultrasonic gas sensors are disposed. The ultrasonic gas sensors adopt different pipeline structures of the hollow pipe, but a spacing between two ultrasonic transducers in one ultrasonic gas sensor is equal to a spacing between two ultrasonic transducers in the other ultrasonic gas sensor. The cross-sectional area of the pipeline of the hollow pipe in the first ultrasonic gas sensor is variable, and the cross-sectional area of the pipeline of the hollow pipe in the second ultrasonic gas sensor is constant. For example, a cylindrical pipeline is adopted. When gases with the same flow and the same flow velocity flow through the pipelines in the two ultrasonic gas sensors, if propagation time differences between forward and backward directions of the two ultrasonic gas sensors are identical, then the cross-sectional area of the pipeline of the second ultrasonic gas sensor is called as the equivalent cross-sectional area of the pipeline of the first ultrasonic gas sensor.

In practical operation, when the to-be-detected gas in the gas chamber does not flow, the microprocessor can measure the average molecular weight of the to-be-detected gas through the first propagation time or the second propagation time. If the to-be-detected gas is a binary gas mixture, the content of each gas (i.e., the concentration of each gas) in the to-be-detected gas can also be further measured. When the to-be-detected gas in the gas chamber flows to a direction at a certain velocity, the microprocessor can use the measured first propagation time and the second propagation time to measure a time difference therebetween, and can further measure the size and the direction of the flow of the to-be-detected gas. If the to-be-detected gas is the binary gas mixture, the content of each gas (i.e., the concentration of each gas) in the to-be-detected gas can also be further measured.

In the present embodiment, the receiving processing circuit 16 amplifies the received signal in a manner of amplitude limiting, and performs "OR" or "AND" operation using a shielding signal and the received signal subjected to amplitude limiting amplification to shield a small-amplitude part in a received signal envelope, so as to detect the arrival time of pulses of a large-amplitude part in the received signal envelope. Preferably, the small-amplitude part in the received signal envelope is a part which is at least smaller than a maximum peak of the received signal envelope by 60%. The received signal subjected to amplitude limiting amplification is shown by C waveform in FIG. 9. The shielding signal is shown by D waveform in FIG. 9. The shielded received signal which is received by the microprocessor 17 is shown by E waveform in FIG. 9.

In the present embodiment, the shielding signal adopts a high-level pulse signal, and the shielding signal and an ultrasonic signal for exciting the ultrasonic transducer are synchronously emitted. Dashed lines in FIG. 9 indicate starting moments of transmission and drive. The shielding signal and the received signal subjected to amplitude limiting amplification perform "OR" operation, and the shielding signal shields the small-amplitude part in the front section of the received signal envelope. The small-amplitude part is the part which is at least smaller than the maximum peak of the received signal envelope by 60%. In practical operation, the front section of the envelope, which is smaller than the maximum peak of the received signal envelope by 80%, can be shielded. By shielding the small-amplitude part in the front section of the envelope of the received signal subjected to amplitude limiting amplification, the microprocessor 17 only begins to detect at maximum amplitude close to the middle section of the envelope, thereby greatly reducing the influence of interfering signals such as noise on a detection result, greatly enhancing a signal-to-noise ratio and ensuring detection accuracy and anti-interference performance of the sensor.

Because the shielding signal is set to shield the small-amplitude part in the received signal envelope, a fixed delay may exist between the arrival time of the pulses of the large-amplitude part in the received signal envelope detected by the microprocessor 17 and the actual propagation time of the ultrasonic signal, i.e., the propagation time detected by the microprocessor 17 is a propagation time with the fixed delay. Because the distance between two ultrasonic transducers, gas temperature and gas molecular weight are certain when the ultrasonic gas sensor is calibrated, the actual propagation time can be determined through computation. During calibration, a pulse in a pulse group that occurs after the shielding signal is designated as a to-be-detected pulse; and the fixed delay between the arrival time of this pulse and the actual propagation time can be determined. In practical detection, the actual propagation time of the ultrasonic signal is obtained by subtracting the above fixed delay from the arrival time of this pulse.

In the present embodiment, to improve the emission intensity of the ultrasonic signal, the ultrasonic transducer is excited to emit the ultrasonic signal by a method of simultaneously and alternately switching the levels of two electrodes of the ultrasonic transducer. In practical operation, the voltage value of a driving signal of the ultrasonic transducer can also be increased so as to increase the emission power. The emission intensity of the ultrasonic wave can also be improved through the combination of the two methods.

In the present embodiment, considering the influence of the temperature on the propagation speed of ultrasonic wave, to improve the measurement accuracy, a temperature sensor 14 used for detecting the temperature of the to-be-detected gas is also disposed. The temperature sensor 14 can be disposed in a groove on an inner cavity wall of the hollow pipe 11 or disposed in any vent. The temperature sensor 14 is connected to the microprocessor 17. The microprocessor 17 can correct a measurement and computation result according to temperature data of the temperature sensor 14.

The ultrasonic gas sensor using the above technical solution has a measurement range of 200 ml/min and a flow accuracy of +/−20 ml/min or higher.

Besides the above embodiments, the present invention can also have other embodiments. Technical solutions formed by adopting equivalent replacement or equivalent transformation shall belong to the protection scope claimed in the present invention.

The present invention has the beneficial effects: compared with a currently launched oxygen generator for respiration-synchronized oxygen supply for detecting the human respiration using a differential pressure sensor, the present invention uses an ultrasonic gas sensor with cheap price and simple and convenient detection technique as a detection element for respiration in the oxygen generator, so that the detection for respiration is realized at low cost and respiration-synchronized oxygen supply is realized, thereby greatly reducing the manufacturing cost of the oxygen generator for respiration-synchronized oxygen supply. Moreover, the ultrasonic gas sensor which is capable of detecting both the gas flow and the oxygen concentration can be adopted, thereby further saving the expense of an oxygen concentration sensor and further reducing the cost of the oxygen generator. The present invention can popularize a respiration-synchronized oxygen supply technique from an expensive portable oxygen generator to a larger number of cheaper desktop oxygen generators, so that the oxygen generator for respiration-synchronized oxygen supply becomes a medical healthcare product that is affordable for ordinary people and is thus popularized and applied more widely.

We claim:

1. An oxygen generator for respiration-synchronized oxygen supply, comprising a control unit for controlling operation of the oxygen generator, an oxygen generating unit, an oxygen supply unit for delivering oxygen provided by the oxygen generating unit to a human body, and an ultrasonic gas sensor for detecting human inhalation or respiration; wherein the oxygen supply unit comprises an oxygen delivery pipeline which is capable of communicating with a human respiratory organ and an oxygen supply valve disposed on the oxygen delivery pipeline; a bypass pipe is communicated to the oxygen delivery pipeline communicated to a gas outlet of the oxygen supply valve; an outer end of the bypass pipe is communicated with a first vent on the ultrasonic gas sensor, and a second vent on the ultrasonic gas sensor is communicated with atmosphere; at least the bypass pipe and part of the oxygen delivery pipeline between the bypass pipe and the human respiratory organ form an airflow forming device configured to form an airflow at least corresponding to human inhalation in the ultrasonic gas sensor during human respiration, so that the ultrasonic gas sensor is enabled to detect at least the human inhalation; the ultrasonic gas sensor is configured to detect both a human inhalation or a respiration airflow and an oxygen concentration of gas outputted by the oxygen generator;

at a starting moment when the oxygen generator begins to operate, the oxygen supply valve is configured to be in a closed state; at least when the human body inhales, the bypass pipe is configured to ensure an inhalation airflow corresponding to the human inhalation formed in the ultrasonic gas sensor, so that the ultrasonic gas sensor is capable of detecting the human inhalation; and during operation, according to data or signals corresponding to the human inhalation detected by the ultrasonic gas sensor, the oxygen supply valve is configured to be open for a set time only when the human body inhales and to be in a closed state at rest, so that the oxygen supply unit supplies oxygen to the human body through the oxygen delivery pipeline only when the human body inhales.

2. The oxygen generator according to claim 1, wherein the second vent on the ultrasonic gas sensor is communicated with atmosphere through a section of pipeline; and in this way, when the oxygen supply valve is closed during operation once oxygen supply is finished, oxygen concentration data detected by the ultrasonic gas sensor at this moment are used as oxygen supply concentration data of the oxygen generator at this moment.

3. The oxygen generator according to claim 1, further comprising a bypass control valve for controlling a communication time between the oxygen delivery pipeline and the atmosphere through the bypass pipe; the bypass control valve is disposed in the bypass pipe; the bypass pipe, the part of the oxygen delivery pipeline between the bypass pipe and the human respiratory organ, and the bypass control valve form the airflow forming device; at the starting moment when the oxygen generator begins to operate, the oxygen supply valve is in the closed state and meanwhile, the bypass control valve is in an open state; in this way, at an initial moment of startup, the bypass pipe ensures the inhalation airflow corresponding to the human inhalation is formed in the ultrasonic gas sensor, so that the ultrasonic gas sensor is capable of detecting the human inhalation; and during operation, once the oxygen supply valve is open and ventilation is completed in the ultrasonic gas sensor, the bypass control valve is closed; and until the oxygen supply valve is closed after the oxygen supply is finished in current cycle, the bypass control valve is open again, so that the bypass pipe ensures that the ultrasonic gas sensor accurately detects each human inhalation and oxygen waste is reduced.

4. The oxygen generator according to claim 3, wherein during operation, if the bypass control valve is closed at a moment, oxygen concentration data detected by the ultrasonic gas sensor at this moment are used as oxygen supply concentration data of the oxygen generator at this moment.

* * * * *